(12) United States Patent
Niemczyk et al.

(10) Patent No.: US 8,101,729 B2
(45) Date of Patent: Jan. 24, 2012

(54) PEGYLATED AMINO ACID DERIVATIVES AND THE PROCESS TO SYNTHESIZE THE SAME

(76) Inventors: Henry Joseph Niemczyk, Wayne, NJ (US); Susan Dorothy Van Arnum, Cranford, NJ (US)

( * ) Notice: Subject to any disclaimer, the term of this patent is extended or adjusted under 35 U.S.C. 154(b) by 844 days.

(21) Appl. No.: 11/688,059

(22) Filed: Mar. 19, 2007

(65) Prior Publication Data

US 2008/0234497 A1    Sep. 25, 2008

(51) Int. Cl.
*C07K 1/06* (2006.01)
*C07K 5/00* (2006.01)

(52) U.S. Cl. .................................. 530/402; 530/323

(58) Field of Classification Search .................. 530/402, 530/323
See application file for complete search history.

(56) References Cited

U.S. PATENT DOCUMENTS

2009/0048147 A1 * 2/2009 Holmes et al. ................ 514/2

FOREIGN PATENT DOCUMENTS

WO   WO 01045796   * 6/2001

OTHER PUBLICATIONS

WO 2001045796 (CAPLUS Abstract accession # 2001:472548).*
Monfardini et al. (Bioconjugate Chemistry (1995), 6(1), 62-9).*
Dent et al. (Org. Lett. (2002), v. 4, n. 8, p. 1249-51).*
Griffith et al. (Abstract of Dermatology, v. 175, No. 4 (1987), 183-90).*
Roberts et. al (Advanced Drug Delivery Reviews 54 (2002) 459-476).*
Griffith et al (Abstract of Dermatology, v. 175, n0 4 (1987), 183-90.
Roberts et. al (Advanced Drug Deliver Reviews 54 (2002) 459-576.
Monfardini et al. (Bioconjugate Chemistry (1995), 6(1),62-9.
Dent et al. (Org Lett (2002). v.4. n,8, p. 1249-51.
VanArnum et al. (Macromolecules (2009), 42 (4), 908-12.

* cited by examiner

*Primary Examiner* — Robert Havlin

(57) ABSTRACT

The present invention is a series of novel pegylated amino acid derivatives containing branched polyethylene glycols, which are either the same or different molecular weights. Additionally, the N-pegylated lysine derivatives are enantiomerically pure. Also disclosed are oligopeptides such as Lysine-Lysine in which the free amino groups are protected as pegylated carbamates. 9-BBN complexes of lysine in which the epsilon nitrogen is functionalized as a pegylated carbamate and Bis pegylated derivatives of multifunctional heteroatom-containing amino acids such as cysteine, serine and glutamic acid are also disclosed.

Figure 1:
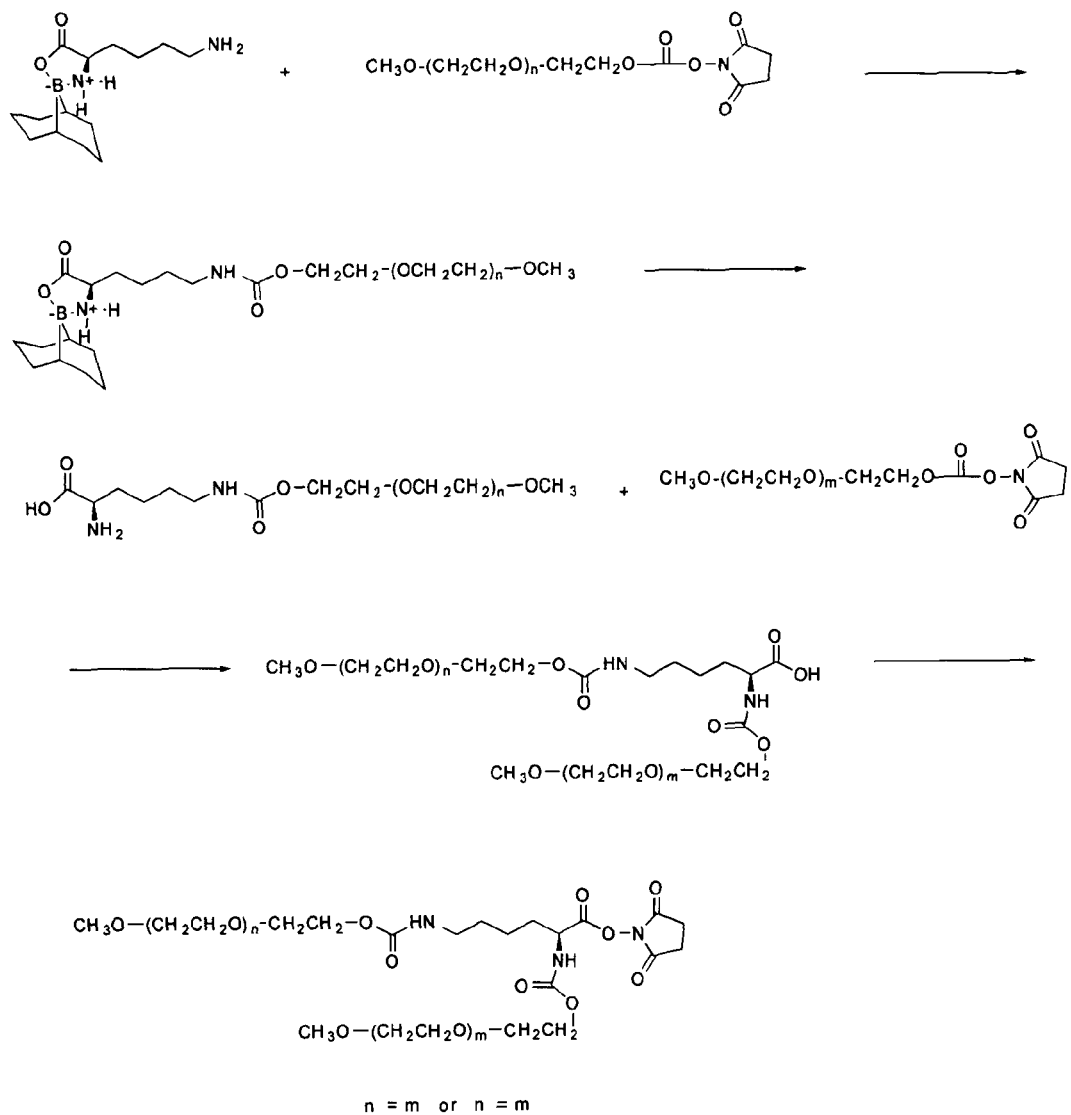

The present invention is also the process to prepare the novel pegylated amino acid derivatives for subsequent reaction with proteins. The process for synthesizing N-pegylated lysine derivatives in which the 9-borabicyclononane (9-BBN) complex of lysine is functionalized as a pegylated carbamate. The process in which the epsilon nitrogen of 9-BBN complex of lysine, which contains a pegylated polymer at the epsilon nitrogen, is hydrolyzed with aqueous hydrochloric acid and a process for synthesizing activated esters of N-pegylated amino acids by esterification of an N-pegylated amino acid are disclosed. A process in which N-epsilon pegylated lysine is reacted with an active pegylated ester is also disclosed.

The novel pegylated amino acid derivatives are new chemical entities (NCE's) not previously described. The processes to prepare these novel pegylated amino acid derivatives have also not previously been described.

3 Claims, 7 Drawing Sheets

1

PEGYLATED AMINO ACID DERIVATIVES AND THE PROCESS TO SYNTHESIZE THE SAME

BACKGROUND OF THE INVENTION

Pegylated (PEG, polyethylene glycol) reagents have been commercialized in order to enhance the desirable properties of protein drugs, peptides, oligonucleotides, antibodies and small molecules. Polyethylene glycol is inert, non toxic and has been approved by the FDA for human administration. There are several pegylated protein drugs on the market including PEG interferon as a treatment for hepatitis, and PEG asparaginase as a treatment for cancer. There are two main types of commercially available PEG reagents, Linear and Branched. In preparing the branched polyethylene glycols from lysine, the resulting lysine derivatives are racemic and the branches have identical peg polymer molecular weights.

The present invention is a novel branched methoxy pegylated lysine derivative in that it is enantiomerically pure, and affords the option for the formation of branched lysine PEGs that have either the same or different molecular weights on each branch. The described enantiomerically pure mPEG derivative has not been reported in the literature, and therefore represents a new chemical entity (NCE). It is prepared from known and commercially available materials, and therefore amenable to commercial manufacturing. Pegylated drugs generally improve the pharmacokinetics and pharmacodynamics of pharmaceuticals. There are many reported advantages of pegylated drugs over non-pegylated drugs, the most important of which are the potential for increased efficacy and lower toxicity. Among the other reported advantages of pegylated drugs over non pegylated drugs are an increase in bioavailability, lower dose levels, increased half life, improved stability, enhanced solubility, sustained absorption, reduced dosing frequency, reduced renal clearance, reduced immunogenicity, reduced antigenicity, reduced proteolysis, and potential for site directed mutagenesis.

As pegylation technology matures and process development improves, the potential to significantly reduce the cost of drugs through reduced dosing requirements will be realized. The potential synergistic effect of drugs can be enhanced through multiple drugs being bound to branched mPEGs. Current drugs not tolerated by patients now have the potential to be tolerated since the dose requirements will be significantly reduced. Through manipulation of the specific drug with a specific molecular weight mPEG, optimization of efficacy can be achieved. The combination of lower dose, less frequent administration, lower toxicity, less side effects, and increased tolerability will improve quality of life for patients. Overall, the potential of pegylated drugs is difficult to overestimate. Through multiple oligopeptide molecules, the potential for a host of new molecular entities (NCEs) exists. Since the safety and efficacy of existing drugs has already been established, pegylation of those drugs which are currently not tolerated for various reasons, have the potential to enhance the desirable pharmacological properties and should result in rapid approvals by the FDA and other regulatory agencies. Due to the resulting low dose levels of pegylated drugs, drugs difficult to obtain will now be more readily available since the amounts for each patient will have been significantly reduced. New chemical entities will have a higher probability of approval due to the lower toxicity and higher efficacy than if they remained non-pegylated. Older drugs previously rejected for toxicity and efficacy reasons now have the potential to be viable drugs and should be reexamined as pegylated derivatives.

This invention has the potential to significantly increase the number of drugs currently available. The mPEG polymerization of drugs will enhance the intellectual property protection afforded through new chemical entity status.

OVERVIEW DESCRIPTION OF THE INVENTION

Since chiral assessment of $(mPEG)_2$-Lysine-NHS, 1, (FIG. 2) is not known, the standard process is likely to produce achiral material as the reaction is done under basic conditions. A truly-valued product and a product differentiator would be to produce chiral $(mPEG)_2$-L-Lysine-NHS.

Since proteins are chiral molecules; (natural amino acids all have the L-designation), a racemic $(m-PEG)_2$-Lysine-NHS reagent will yield to diastereotopic proteins in the active drug substance.

In the literature, the use of boron complexes of amino acids to increase their solubility in organic solvents is well known. A relatively recent publication in *Organic Letters* (2002) showed that the 9-BBN-complexes of polysubstituted amino acids such as lysine are readily soluble in organic solvents and that their preparation is straightforward. Although this paper showed that 9-BBN-L-Lysine is not appreciable soluble in methylene chloride, sufficient molecular solubility coupled with the high reactivity of amines (the epsilon nitrogen in 9-BBN-Lysine) should allow for the nucleophilic reaction to occur.

Consequently, when a lysine derivative is solubilized, the coupling reaction will occur and in fact BBN-L-Lysine readily reacted with m-PEG-SC in methylene chloride. The standard method of product analysis, $^{13}C$ NMR is compromised to some extent by $^{13}C-^{11}B$ coupling. The known literature insolubility of BBN-L-Lysine in methylene chloride and the observed reaction solubility indicated that the desired reaction had indeed occurred.

Figure 4:
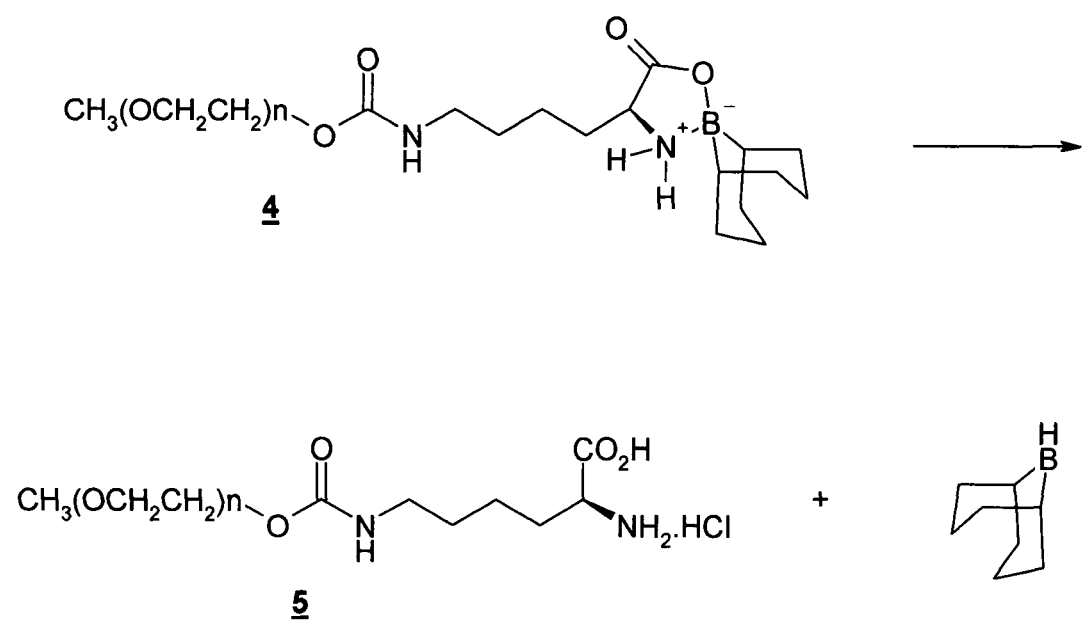

As shown in FIG. 4, hydrolysis of mPEG-BBN-L-Lysine, 4, as per a modified literature procedure in a mixture of methanol and aqueous hydrochloric acid yielded the correct product.

Figure 5:
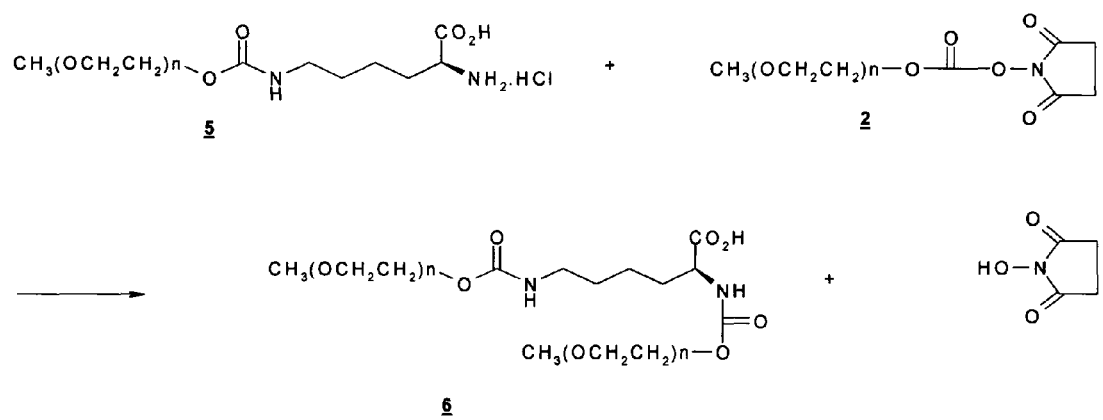
Figure 6:
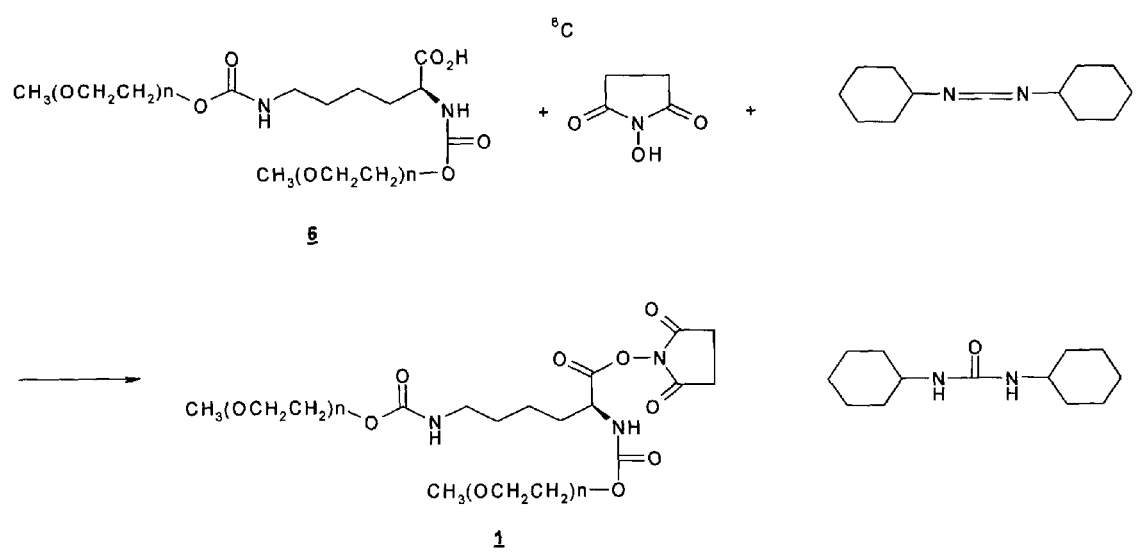
Figure 7:
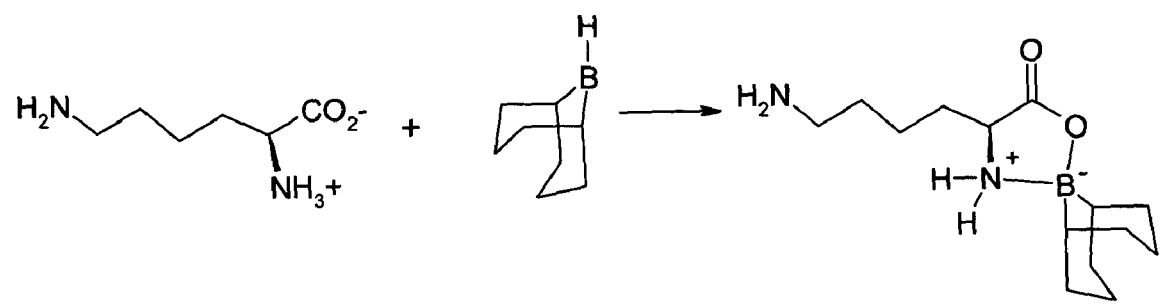

The isolated product is as the hydrochloride salt of mPEG-L-Lysine 5. As shown in FIG. 5, the hydrochloride salt was free-based and the addition of a second mole of mPEG-SC yielded the correct product 6.

The standard ethyl acetate purification afforded the pure $(mPEG)_2$-L-Lysine 6.

Characteristics of 9-BBN-Lysine Process

No Chromatographic separations are required.
No laborious product extractions with methylene chloride are necessary.
Optically active $(mPEG)_2$-L-Lysine is produced.
Same or different mw PEGs can be produced

BRIEF SUMMARY OF THE INVENTION

Figure 2:
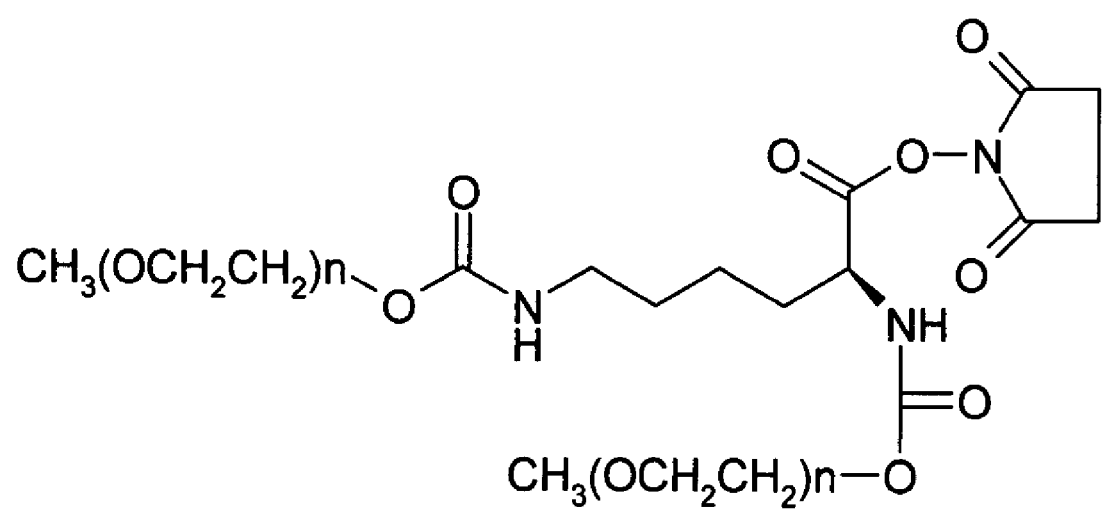
Figure 3:
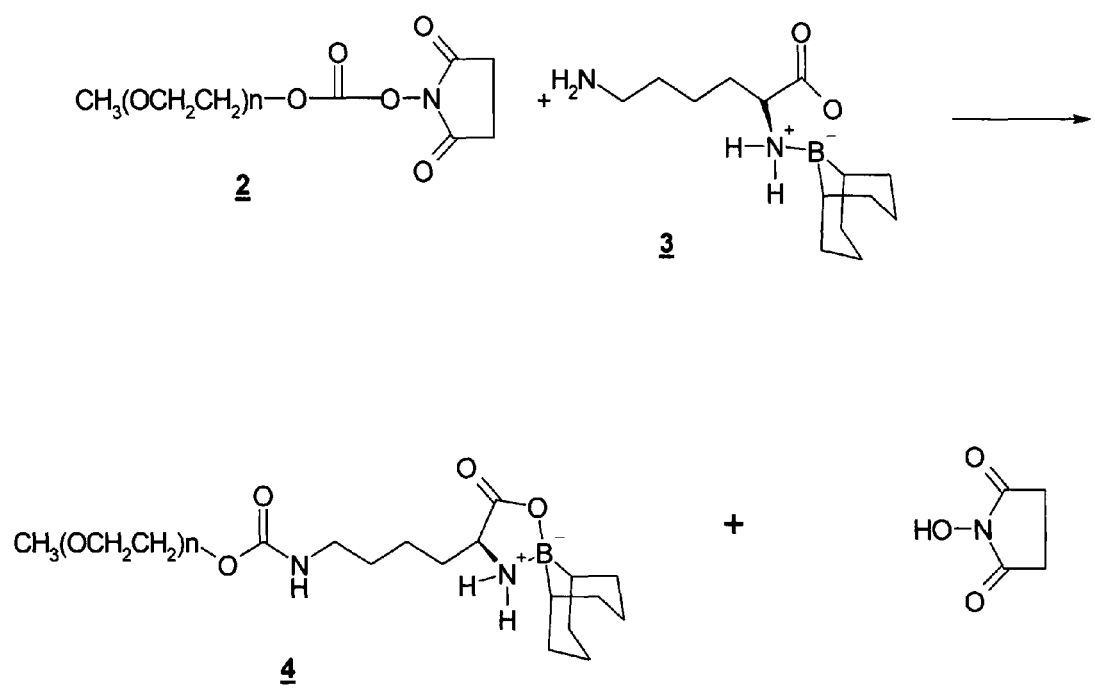

FIG. 1 depicts the chemical reaction steps to produce branched PEG lysine activated reagent. Reacting BBN lysine with PEG-SC to form PEG BBN Lysine. Removal of the BBN and reacting with another mole of PEG-SC results in a branched PEG Lysine acid. Further reaction with N hydroxyl succinimide results in the activated branched PEG Lysine. FIG. 2 represents the structure of an enantiomerically pure branched activated PEG with identical 20 kDa PEGs. FIGS. 3 through 7 depict a detailed example of the chemistry used to synthesize the enantiomerically pure branched activated PEG reagent. The present invention is the new chemical entity since it is enantiomerically pure. Additionally, as described in claim 1, if two different molecular weight PEGs are used, the resulting branched PEGs are novel compounds since only same molecular branched PEGs have been previously described. What is also claimed is the process for synthesizing these compounds.

The invention claimed is:

1. A process for making essentially enantiomerically pure N-pegylated amino acids and oligopeptides, comprising:
   a. reacting 9-borabicyclononane complexes of essentially enantiomerically pure amino acids and oligopeptides with a pegylated activated ester to produce a monopegylated product;
   b. deprotecting said monopegylated product to produce a deprotected monopegylated product; and
   c. reacting said deprotected product with a pegylated activated ester.

2. The process of claim 1 wherein the amino acids are essentially enantiomerically pure lysine or cysteine.

3. The process of claim 1 wherein the pegylated activated esters are succinimido carbonates.

* * * * *